United States Patent [19]

Beaumont et al.

[11] Patent Number: 5,264,372
[45] Date of Patent: Nov. 23, 1993

[54] RECEPTOR-BASED SCREENING METHODS FOR AMYLIN AGONISTS AND ANTAGONISTS

[75] Inventors: Kevin Beaumont; Timothy J. Rink, both of San Diego, Calif.

[73] Assignee: Amylin Pharmaceuticals, Inc., San Diego, Calif.

[21] Appl. No.: 670,231

[22] Filed: Mar. 15, 1991

[51] Int. Cl.$^5$ ................. G01N 33/566; G01N 33/567
[52] U.S. Cl. .................................. 436/504; 436/501; 436/503
[58] Field of Search ..................... 436/501, 503, 504

[56] References Cited

U.S. PATENT DOCUMENTS 4,434,236 2/1984 Freytag ............................. 436/572

FOREIGN PATENT DOCUMENTS 0408294 1/1991 European Pat. Off. .
8906135 7/1989 World Int. Prop. O. .

OTHER PUBLICATIONS

Morishita et al (1990 Jul.) Diabetes 39:875–877.
Stephens et al (1991 Mar.) Diabetes 40:395–400.
Sayema et al (1975) Fertility & Sterility 26:397–404.
Clark et al (1987) Lancet 8554:231–234.
Leighton et al (1988) Nature 335:632–635.
Sanke et al (1988) J. Biol Chem 263:17243–17246.
Leighton et al (1990) Biochem J 269:19–23.
Leighton et al (1990) TIBS 15:295–299.
Cooper et al., Proc. Nat'l Acad. Sci. USA 84:8628–32 (1987).
Cooper et al., *Prog. Growth Factor Research* 1:99–104 (1989).
Rosenfeld et al., *Nature* 304—129–35 (1983).
Amara et al., *Science* 229—1094–97 (1985).
Leighton et al., Nature 335:632–35 (1988).
Young et al., *Amer. J. Physiol.* 259:E457–61 (1990).
Leighton et al., *Biochem. J.* 269:19–23 (1990).
Young et al., *FEBS* 281:149–51 (1991).
Molina et al., *Diabetes* 39:260–65 (1990).
Koopmans et al., *Diabetes* 39:101A (1990).
Ciaraldi et al., *Diabetes* 39:145A (1990).
Brain et al., *Amer. J. Pathol.* 136:487–90 (1990).
Datta et al., *Biochem. Biophys. Res. Commun.* 162:876–80 (1989).
Chantry et al., *Biochem. J.* 277:139–43 (1991).
Banks, *Journal of NIH Research* 2:34–35 (1990).
Banks, *Diabetes Forecast* 44:26–31 (1991).
Tschopp et al., Proc. Nat. Acad. Sci. USA 82:248–52 (1985).
Sexton et al., *Neuroscience* 19:1235–45 (1986).
Goltzman et al., *Science* 227—:1343–45 (1985).
Sexton et al., *Kidney Int.* 32:862–68 (1987).
Sexton et al., *Neurochem. Int.* 12:323–35 (1988).
Dennis et al., *Soc. Neurosci. Abs.* 16:514 (1990).
Galeazza et al., *Peptides* 12:585–91 (1991).
Dennis et al., *Journal of Pharmacology and Experimental Therapeutics* 251:718–725 (1989).
Dennis et al., *Journal of Pharmacology and Experimental Therapeutics* 254:123–128 (1990).
Dennis et al., *Brian Research* 539—59–66 (1991).
*Trends in Pharmacological Sciences Receptor Nomenclature Supplement*:10 (Jan. 1992).

*Primary Examiner*—Christine M. Nucker
*Assistant Examiner*—David R. Preston
*Attorney, Agent, or Firm*—Lyon & Lyon

[57] ABSTRACT

Methods for identifying or screening or characterizing or assaying or isolating known or candidate agonists and antagonists of amylin, comprising binding assays utilizing preparations containing specific receptors for amylin. Membranes from the brain that contain high density receptors for amylin are particularly useful for the methods of this invention, and as a source of amylin receptors.

63 Claims, 5 Drawing Sheets

RECEPTOR-BASED SCREENING METHODS FOR AMYLIN AGONISTS AND ANTAGONISTS

FIELD OF THE INVENTION

The present invention relates to methods for identifying physiologically active materials, such as chemical compounds, by assessing their ability to interact with naturally occurring or isolated or cloned receptor sites. More particularly, the invention relates to methods for identifying agonists and antagonists for amylin, and related peptide hormones useful in regulating the effects of insulin, involving assessing the ability of candidate compounds to bind to certain biologic preparations containing receptors for amylin.

DESCRIPTION OF THE RELATED ART

Resistance to insulin may be present in several serious disorders, including Type 2 diabetes mellitus, obesity and hypertension. Resistance to insulin is manifested by reduction in the effectiveness of a given dose of insulin compared to that obtained in a non-resistant state. Thus, in an insulin-resistant patient with Type 2 diabetes mellitus, the ability of both endogenous insulin and insulin administered exogenously to control the chronic hyperglycemia suffered by such patients is seriously compromised. Consequently, the complications that result from uncontrolled diabetes mellitus, such as premature atherosclerosis, intercapillary glomerulosclerosis, retinopathy, neuropath a kidney failure, are more likely to occur in insulin-resistant diabetics than in insulin-sensitive diabetics. In clinical terms insulin resistance is present when normal or elevated glucose concentrations persist in the face of normal or elevated concentrations of insulin in the general circulation. Insulin resistance represents, in essence, inhibition of glycogen synthesis from metabolic precursors due to a reduction to subnormal levels of either basal or insulin-stimulated glycogenesis, or both.

There are at least two causes of hyperglycemia in Type 2 diabetes mellitus: (1) failure of glucose storage to be activated (Lillioja, S., *J. Clin. Endocr. Metab.*, 62:922-927 (1986)); and (2) a defect in insulin release from the pancreas (Waingot, A., et al., *Proc. Nat'l Acad. Sci. USA.* 79:4432-4436 (1982)). Treatment of this disease has focused on attempts to reverse either or both of these defects.

Recently, a novel protein hormone isolated from the pancreas has been shown to modulate certain of the actions of insulin. The hormone, termed amylin (initially referred to as diabetes associated peptide or DAP), was recently purified to homogeneity from pancreatic amyloid from human Type 2 diabetes mellitus patients. E.g., Cooper, G. J. S., et al., *Proc. Nat'l Acad. Sci. USA*, 84:8628-8632 (1987). Amylin is the subject of United Kingdom patent application Serial No. 8709871, filed Apr. 27, 1987, and corresponding U.S. applications filed Apr. 27, 1988, Nov. 23, 1988 and May 2, 1989. The use of amylin for the treatment of diabetes mellitus is the subject of United Kingdom patent application Serial No. 8720115 filed on Aug. 26, 1987, by G. J. S. Cooper et al., and filed in the United States on Aug. 26, 1988.

Native amylin is a 37 amino acid protein characterized by a disulfide bridge between the Cys residues at positions 2 and 7 and an amide group at the C-terminal tyrosine. The amylin subpeptide 18-27 is amyloidogenic, that is, it possesses the tendency to form amyloid. The structure of amylin shows a 43% homology to calcitonin gene related peptide-1 (CGRP-1), a 46% homology to CGRP-2, and some similarity to insulin. Amylin may be one member of a family of related peptides which include CGRP, insulin, insulin-like growth factors, and the relaxins and which share common genetic heritage. Cooper, G. J. S., et al., *Prog. Growth Factor Research* 1:99-105 (1989). See Amara, S. G., et al., *Science*, 229:1094-1097 (1985); Rosenfeld, M. G., et al., *Nature*, 304:129-135 (1983). The two peptides calcitonin and CGRP-1 share common parentage in the calcitonin gene where alternative processing of the primary mRNA transcript leads to the generation of the two distinct peptides, which share only limited sequence homology (about 30%). Amara, S. G. et al., *Science*, 229:1094-1097 (1985).

It has been disclosed in commonly-owned International Application No. PCT/US89/0049, published Jul. 13, 1989 (International Publication No. WO89/06135), and filed Jan. 11, 1989 by Cooper, G. J. S. et al., the contents of which are incorporated herein by reference, that amylin causes reduction in both basal and insulin-stimulated incorporation of labelled glucose into glycogen in skeletal muscle. The latter effect was also disclosed to be shared by CGRP. See also Leighton, B. and Cooper, G. J. S., *Nature*, 335:632-635 (1988). Amylin and CGRP were approximately equipotent, showing marked activity at 1 to 10 nM. Amylin is also reported to reduce insulin-stimulated uptake of glucose into skeletal muscle and reduce glycogen content. Young et al., *Amer. J. Physiol.* 259:457-461 (1990). Amylin is further said to, in certain circumstances, increase lactate release from skeletal muscle. Leighton, B. and Foote, E., *Biochem J.* 269:19-23 (1990).

It is believed that the amylin family of peptide hormones acts through receptors present in plasma membranes. We have shown that amylin works in skeletal muscle via a receptor-mediated mechanism that promotes glycogenolysis, by activating the rate-limiting enzyme for glycogen breakdown, phosphorylase a (Young, A. et al. 1991 FEBS Letter in press).

The major metabolic effects of amylin reported in vivo are: (1) a reduction in insulin action observed under "euglycemic clamp" conditions whereby infusion of amylin reduces insulin mediated glucose clearance (Molina et al. Diabetes 39:260-265 (1990) and Young et al, Am. J Physiol, 259:457-461 (1990)) and partly reverses insulin-mediated suppression of hepatic glucose output (Molina et al. supra; Koopmans, J. J., et al. Diabetes 39:101A (1990)); (2) In lightly anaesthetized, 18-hour fasted rats, bolus injections of amylin evoke first an increase in plasma lactate, and second a sustained increase in plasma glucose. The increase in plasma lactate is thought to reflect lactate production in skeletal muscle, consequent upon amylin stimulation of glycogenolysis. This action of amylin is observed in the fed as well as the 18-hour fasted rat, and also during somatostatin infusion given to limit secretion of pancreatic hormones including insulin and glucagon. These data substantiate the determination that amylin acts independent of other hormonal regulators to promote lactate release from skeletal muscle in intact animals.

The increase in plasma glucose is associated with a dilution of infused trace glucose, indicating increased hepatic glucose output. It is not presently known whether the actions of amylin infusion in "euglycemic clamped" rats, and amylin injections, to increase hepatic glucose output is a result of direct actions of amylin on liver, or an indirect effect of the amylin actions, such as the release of lactate from muscle. For instance, it was reported that amylin increases gluconeogenesis and glycogenolysis in cultured Hep G2 cells (a cell line derived from a human liver tumor). Ciaraldi et al., Diabetes 39: Supp. 1, 145A (1990). On the other hand, it was reported that amylin had no observable effects on glucose metabolism in isolated rat hepatoyctyes or in perfused rat liver (Stephens et al. Diabetes in press 1991).

It is also reported that amylin can exert certain other actions in vivo, including vasodilatation. Brain S. D. et al. Am. J. Pathol. 136:487–490 (1990). Amylin was 100 to 1000 fold less potent as vasodilator than the related peptide CGRP. This could reflect a weak action of amylin on CGRP receptors although no evidence was provided in support of this. Amylin is also reported to lower plasma calcium in rabbits and rats (Datta H. K. et al. Biochem. Biophys. Res. Commun. 162:876-881 (1989)). This action resembles that of calcitonin. Human calcitonin was more effective than amylin in adducing hypocalcaemia and it is possible, though also unproven, that amylin acts less potently than calcitonin at calcitonin receptors on bone cells.

It is believed that CGRP and calcitonin act via membrane receptors at least some of which serve to activate adenylate cyclase and generate cyclic AMP as an intracellular second messenger. In this regard, high affinity binding sites (receptors) for CGRP on liver membrane were reported; at these sites CGRP is said to potently activate adenylate cyclase. E.g. Morishita, et al. Diabetes 39:875-877 (1990). Amylin was reported to displace labelled CGRP from these binding sites but with much lower affinity, approximately 300 nM, than CGRP, approximately 9 pM. Somewhat similar findings are reported by Chantry et al., Biochem J. in press 1991); these authors report apparent affinities for CGRP and amylin on liver membranes of approximately 100 to 300 pM and IOnM respectively. Chantry et al. point out that liver contains very little CGRP, and that amylin is secreted from the portal vein directly supplying the liver. They propose that the glucose regulatory role of these peptides in hepatic metabolism may be mediated primarily by amylin. However, Chantry, et al. were not able to measure amylin binding to liver membranes. Stephens et al., supra, were able to measure CGRP and amylin binding to a preparation of liver cell membranes; however, from studies of separated parenchymal and interstitial liver cells they concluded that the main binding was to interstitial cells and that the lack of binding to parenchymal cells was consistent with a lack of amylin action on hepatocyte metabolism. Thus, the question of the nature and even existence of functionally relevant amylin receptors on liver is confused and unresolved. Indeed, the existence of an amylin receptor or receptors has been questioned by some, while still others perceive that such a receptor will someday be identified (Banks, P. Jornal of NIH Research 2:34-35 (1990); Diabetes Forecast, March 1991, 27-31).

Thus far, there is only one report of studies seeking amylin receptors in skeletal muscle. Chantry et al. report that CGRP and amylin compete for $^{125}$I-CGRP binding to crude membrane preparations, CGRP with an $IC_{50}$ of 300 pM and amylin with an $IC_{50}$ of 10 nM. They suggest that these data are indicative of a common system for mediation of the action of both peptides on skeletal muscle. However, this appears inconsistent with the fact that in functional studies of skeletal muscle, amylin is somewhat more potent than CGRP, not 30 times less potent as found in the reported binding studies.

It will be apparent then, that while several investigators have postulated and/or sought receptors that could mediate the metabolic actions of amylin, none have been identified. From the available binding data and the cardiovascular responses reported by Brain et al. one could speculate only that the high affinity receptor reported in liver membranes is that which mediates the potent vasodilator effects of CGRP and that amylin may exert its much weaker vasodilator responses via this receptor. This receptor is appropriately designated a CGRP receptor, and may be type of receptor in skeletal muscle membranes that was investigated by Chantry et al.

Binding sites for calcitonin and CGRP are widely distributed in the central nervous system. However, the two peptides act at their own distinct high affinity receptors with distinct biochemical specificities and little interaction at the alternate receptor site. Sexton, P. M. et al. (1988), Neurochem. Int., 12:323-335 (1988). For example, it has been reported that in both human (Tschopp, F. A. et al., Proc. Nat. Acad. Sci. USA 82:248-252 (1985)) and rat (Sexton, P. M. et al., Neuroscience 19:1235-1245 (1986)) cerebral cortex, calcitonin was 500-1000 fold less potent than either rat or human CGRP in competition for CGRP binding sites. Similarly, CGRP was 500-1000 fold less potent in competing for calcitonin sites in both brain and renal membranes (Goltzman and Mitchell, Science 227:1343-1345 (1985)), as well as in whole kidney sections (Sexton, P. M. et al., Kidney Int. 32:862-868 (1987)). Some data regarding atypical CGRP binding sites in regions of the rat brain have been reported. Dennis, T., et al., Soc. Neurosci. Abs. 16:514, Abstract 220.7 (1990); Sexton, P. M. et al., Neurochem. Int. 12:323-335 (1988). High densities of binding sites with high affinity for the two otherwise biochemically distinct peptides salmon calcitonin and CGRP α were reported to have been identified by the use of autoradiographic techniques in parts of the ventral striatum, including posterior nucleus accumbens (except for a small medial band associated with the shell of the accumbens) and its caudal continuation with the posteriocaudal caudate putamen and posterior fundus striati, as well as the lateral border of the lateral bed nucleus of the stria terminalis and the medial nucleus of the amygdala. Sexton, P. M. et al. (1988), supra. Outside the basal ganglia related nuclei, the organum vasculosum of the lamina terminalis, wings of the dorsal raphe, and area postrema were the only reported regions where calcitonin-sensitive CGRP binding was identified by Sexton et al.

Currently, amylin agonist activity is assessed by measuring the inhibition of insulin-stimulated glycogen synthesis in intact rat soleus muscle. Leighton et al. (1988) supra. While effective as a quantitative biological assay, this technique is relatively slow, labor-intensive and is sensitive to the effects of cellular proteolytic enzymes on the peptides being tested. The soleus assay is effective in quantitating relative potencies of agonists but the affinity of a ligand for its receptor cannot accurately be determined from agonist dose-response relations in whole tissues or organs. For instance, different molecular sizes, or solubility, or propensity to bind to tissue components can influence the defined potencies. The soleus assay, furthermore, has little or no value as an effective, high-throughput primary screening assay for compounds active at amylin receptors. Further methods for screening potential amylin and related peptide hormone agonists and antagonists for clinical use that are inexpensive, rapid and based on physiological principles would be highly desirable. Such methods have been discovered and are disclosed below.

SUMMARY OF THE INVENTION

The invention comprises rapid, inexpensive and physiological methods for identifying, screening and characterizing potential amylin agonists and antagonists for therapeutic usefulness, comprising assessing the ability of such candidate molecules to compete against tracer concentrations of certain labeled peptides, including certain labeled peptide hormones and fragments and analogs thereof, for binding to specific receptor binding sites in cells or membranes prepared or isolated from said cells or from tissues containing cells with membrane receptors for amylin. Amylin receptors can be identified by a binding affinity for Bolton-Hunter $^{125}$I-labelled rat amylin of between about 20 and about 50 pM under conditions of magnesium-free and low salt, or displacement of this amylin label by other ligands.

In one aspect, the invention provides for an assay method for use in identifying or screening for agonists or antagonists of amylin, which includes bringing together a test sample and an amylin receptor preparation, the test sample containing one or more test compounds, and the amylin receptor preparation containing an amylin receptor protein capable of binding to amylin; incubating the test sample and the receptor preparation under conditions that allow the binding of amylin to the receptor protein; and, identifying those test samples containing one or more test compounds which detectably bind to the receptor protein. In another embodiment, this method further comprises the steps of screening test samples which detectably bind to the receptor protein for in vitro or in vivo stimulation or inhibition of amylin receptor mediated activity, and identifying those test samples which act as agonists or antagonists of amylin. In a preferred embodiment, the test samples which detectably bind to the amylin receptor protein are identified by measuring the displacement of a labeled first ligand from the receptor protein preparation by the test sample, and comparing the measured displacement of the first labeled ligand from the receptor preparation by the test sample with the measured displacement of the labeled first ligand from the receptor preparation by one or more known second ligands. Labeled first ligands and second ligands include amylin, an amylin agonist, or an amylin antagonist. Useful receptor preparations include isolated cells bearing the amylin receptor, isolated membrane preparations bearing the amylin receptor and isolated amylin receptor protein. When isolated membranes are used as the receptor preparation, especially preferred are membranes from the basal forebrain region. Test samples used in any of the above methods that contain more than one test compound and which yield positive results can then be divided and retested as many times as necessary, and as appropriate, to identify the compound or compounds in the test sample which are responsible for yielding the positive result.

In another aspect, the invention provides for an assay method for evaluating one or more receptor binding characteristics sought to be determined for a known or a candidate amylin agonist or antagonist compound, which includes the steps of assessing or measuring the ability of the compound to compete against a labeled ligand for binding to an amylin receptor preparation; assessing or measuring the ability of the compound to compete against the labeled ligand for binding to a CGRP receptor preparation, or assessing or measuring the ability of the compound to compete against the labeled ligand for binding to a calcitonin receptor, or assessing or measuring the ability of the compound to compete against the labeled ligand for binding to a CGRP receptor preparation and to a calcitonin receptor preparation; and, determining the receptor binding characteristic sought to be determined for said compound. Receptor binding characteristics which may be determined include binding affinity and binding specificity. CGRP receptor preparations include hepatocyte preparations, including primary cell cultures or established cell lines. Calcitonin receptor preparations include cell or membrane preparations bearing the Cl receptor.

In still another aspect, the invention provides for an assay method for determining the presence or amount of an amylin receptor binding compound in a test sample to be assayed, which includes the steps of bringing together the test sample and an amylin receptor preparation; measuring the ability of the test sample to compete against a labeled ligand for binding to the amylin receptor preparation; and, optionally, relating the amount of amylin receptor binding compound in the test sample with the amount of amylin receptor binding compound measured for a negative control sample, the negative control sample being known to be free of any amylin receptor binding compound, and/or relating the amount of amylin receptor binding compound in the test sample with the amounts of amylin receptor binding compound measured for positive control samples which contain known amounts of amylin receptor binding compound, in order to determine the presence or amount of amylin receptor binding compound present in the test sample. This assay method, in still further embodiments, can be utilized to evaluate the stability of an amylin preparation, to evaluate the potency of an amylin preparation, and to evaluate the solubility characteristics of an amylin preparation.

In another aspect, the receptor preparations of the invention can be utilized to prepare anti-amylin receptor antibodies, including polyclonal antisera and monoclonal antibodies, utilizing art-known methods.

In another aspect, the invention is used to screen cell lines, cells desegregated from tissue, and cells from human or amylin blood in order to identify those which carry animal receptors. The amylin receptor preparations of the invention may also be bound to a solid phase and used in various affinity chromatography methods and used, for example, for the purification of amylin or the evaluation of samples known or suspected to contain amylin, amylin agonists or amylin antagonists.

It is thus an object of this invention to identify receptor preparations suitable for the screening method of this invention.

It is another object of this invention to provide details of the screening methods of the invention as applied to potential agonists and antagonists of amylin.

It is still another object of this invention to teach the method for assessing the relative potencies and specificities of the candidate agonists and antagonists.

It is still another object of the invention to provide a method, using amylin receptor preparations, for determining the presence or amount of amylin and other molecules that bind to the amylin receptor.

These and other objects will become readily apparent by reference to the specification and the appended claims.

LEGENDS TO FIGURES

FIG. 1 shows a Scatchard plot of saturation binding of $^{125}$I-h CGRP to rat liver membranes. $^{125}$I-h α-CGRP concentration was varied from 1.3 to 150 pM. Nonspecific binding was measured in the presence of $10^{-7}$M h α-CGRP. Kd=19.1 pM, Bmax=49.4 fmol/mg protein.

Figure 5:
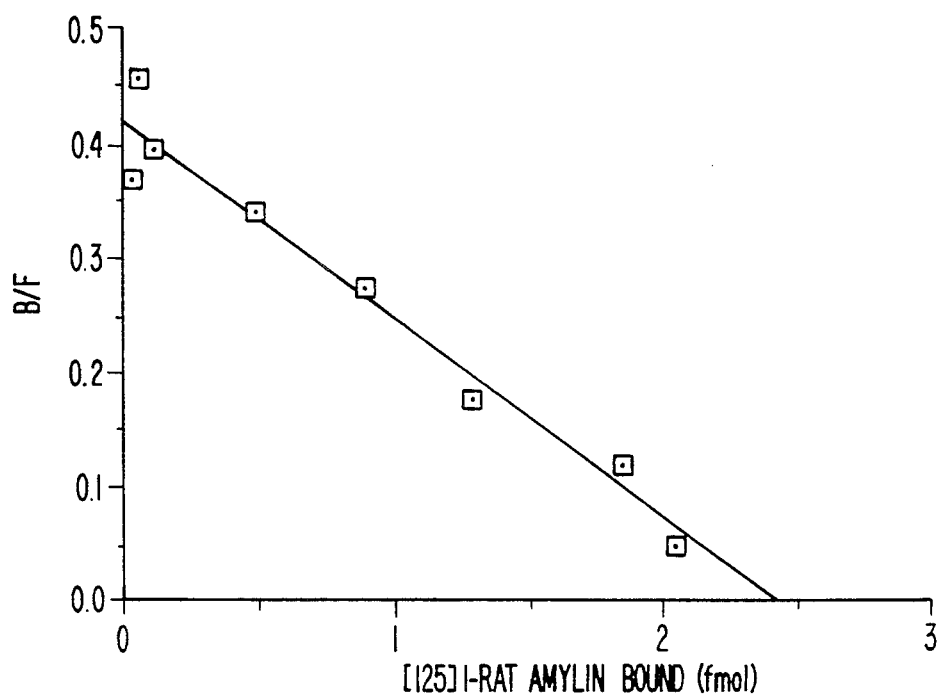

FIG. 5 shows a Scatchard plot of saturation binding of $^{125}$I-r amylin to rat basal forebrain membranes. Binding of increasing concentrations of rat amylin to membranes prepared from 2.5 mg tissue was measured. Nonspecific binding was measured in the presence of 100 nM salmon calcitonin. Kd=27.1±2.1 pM, Bmax=0.98±0.096 fmol/mg (n=3).

Figure 6:
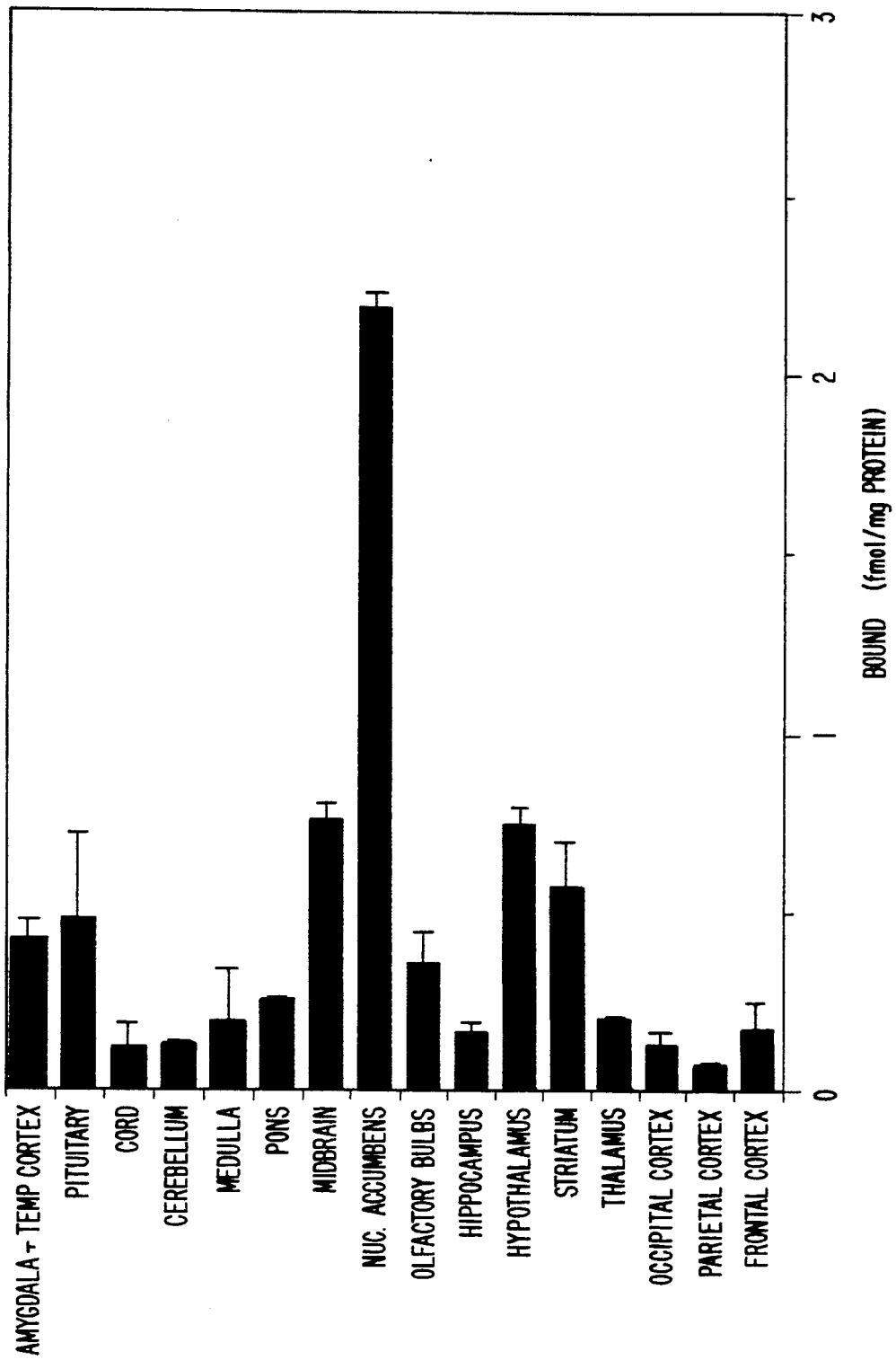

FIG. 6 shows the binding of $^{125}$I-r amylin to rat brain regions. Specfic binding of $^{125}$I-r amylin was measured at a concentration of 17 pM. Nonspecific binding was measured in the presence of 25 nM r amylin.

DETAILED DESCRIPTION OF THE INVENTION

The present invention provides novel inexpensive, rapid and physiological methods for screening, identifying, and characterizing potential agonists and antagonists of the physiological actions of the peptide hormone amylin, which comprises assessing the relative abilities of candidate agonists and antagonists to compete against relevant peptides for binding to specific amylin receptor sites. The receptor sites used for these and other purposes may be present as isolated receptor-bearing tissues, cells prepared from said receptor bearing tissues, membrane preparations derived from said cells, and isolated receptor protein preparations including cloned receptor preparations using recombinant DNA techniques.

There is general agreement that the term "receptor" or "specific receptor" refers to a macromolecule capable of recognizing and selectively binding with some ligand, and which, after ligand binding, is capable of generating some physical or chemical signal that initiates the chain of events leading to the physiological response. Blecher, M., et al., "Receptors and Human Disease", Williams & Wilkins, Baltimore, 1981, Chapter 1. It is thus an important part of this invention that the tissue, cells, membrane, or receptor preparations used in the competition-based screening methods of the invention exhibit binding characteristics of a natural receptor.

Tissue preparations or cell preparations derived from target tissues of the physiological actions of amylin have been identified for use in methods for screening amylin antagonists and agonists, but are inferior to the methods of this invention. Unexpectedly, we have found that cells or membranes bearing the amylin receptor, or amylin receptor protein preparations, are preferably isolated from regions of the brain. See Blecher, M., ed. "Methods in Receptor Research," vols. 1 and 2, Marcel Dekker, New York, 1976; Boulton, A. A. et al., eds., "Neuromethods For Receptor Binding," Humana Press, Clifton, N.J., 1986.

Basal forebrain membranes, comprising membranes from the nucleus accumbens and surrounding regions, are preferred for several reasons. Firstly, as detailed below, a high affinity binding site for amylin is present at high density in the basal forebrain, as well as in other brain regions; specific binding of labeled amylin to such membranes accounted for at least 70% of total binding, indicating the specificity and abundance of the sites. Secondly, also as shown below, the relative potencies of three peptides tested for binding to these membranes (rat amylin > CGRP > CGRP$_{8-37}$) is similar to their relative potencies in altering soleus muscle glycogen metabolism, and is quite distinct from their relative potency at inhibiting labeled CGRP binding to receptors in liver and L6 myocyte membranes. We have determined that the high affinity receptor measured in the rat basal forebrain is also present in soleus muscle at levels not readily detected by current methods and is the preferred target of interest for amylin agonist and antagonist drug development.

Effects produced by infusion into the brain of either CGRP or calcitonin include reduction of amphetamine-induced locomotor activity (de Beaurepaire, R. et al., *Pharm. Biochem. Behav.* 27:177 (1987); reduced food intake (Cooper, C. W., et al., *Psychopharm. Bull.* 20:451 (1984); reduction in growth hormone released (Tannenbaum, G. S., et al., *Endocrinol.* 116:2685 (1985); inhibition of gastric acid secretion (Lenz, H. J., et al., *Gastroenterol.* 88:539 (1985); and inhibition of growth hormone secretion (Fahim, A., et al., *Neuroendocrinol.* 51:688 (1990).

Membrane preparations containing amylin receptors suitable for assay and screening purposes can be identified as follows: (1) $^{125}$I Bolton Hunter rat amylin binding has under the conditions specified herein, particularly lack of magnesium, and salt concentration up to 50 mM, a Kd between about 15 pM and about 60 pM; (2) the displacement of about 10 to 15 pM labelled amylin by other ligands has IC$_{50}$ values of: rat amylin, about 20 to 40 pM; eel calcitonin, about 20 to 50 pM; salmon calcitonin, about 25 to 60 pM; rat β-CGRP about 50 pM to 100 pM; human β-CGRP about 100 pM to 200 pM; human α-CGRP, about 130 pM to 230pM; rat α-CGRP, about 250pM to 550pM; 8-37human CGRP, about 1 nM to 5 nM; human calcitonin, about 2 to 10 μM. It will most typically be preferred to select only certain ligands to establish the presence of amylin receptors for instance, one of rat amylin or salmon calictonin and one of human α-CGRP or human β-CGRP and 8-37human α-CGRP.

In general, tissue membranes are prepared by brief (4–10 seconds) homogenization of tissues at ice bath temperatures at a buffered pH of about neutrality. In one embodiment, an instrument such as a Polytron (Brinkman Instruments, N.Y.) is used, although other similar homogenizers may also be used. Following tissue disruption, membranes are isolated in the cold at g-forces of at least about 20,000×g for an appropriate time, preferably above 40,000×g for at least 10 minutes. Membranes are normally washed at least twice by re-homogenization in fresh buffer, and reisolated as above, in order to remove endogenous interfering substances. Washed membranes are resuspended in buffer containing a proteolytic enzyme inhibitor such as phenylmethylsulfonyl fluoride (PMSF) or bacitracin. Volumes of buffer may be added sufficient to adjust the final tissue concentration to a level suitable for the particular screening method embodiment employed.

Incubation mixtures for the screening method are set up as follows. To glass or polymeric tubes are added a small volume of Buffer Mixture ("HBBM") composed of a buffer solution such as HEPES containing a protease inhibitor such as bacitracin or PMSF, protease-free serum albumin (preferably fraction V BSA, protease-free) and, optionally, a $Mg^{2+}$ salt. To this Buffer Mixture is added a small volume of buffer containing the unlabeled molecules to be tested for agonist or antagonist activity at concentrations of about from $10^{-11}$ to $10^{-6}$ M. Control tubes contain buffer alone. To this mixture is added amounts of labeled amylin or CGRP or calcitonin in buffer so as to produce final concentrations of from about 10 to about 16 pM. Because of the high specific activities obtainable and ease of chemical labeling, $^{125}I$ is preferred to label the peptide hormones. The peptide hormones may be isolated from human tissues (and termed, e.g., "h CGRP" or "h amylin" wherein "h" stands for human), from animal tissues (e.g., salmon calcitonin, i.e., s calcitonin, or rat amylin, i.e., r amylin), or produced by chemical synthetic or recombinant means. $^{125}I$-h CGRP (labeled at $^{10}His$) and $^{125}I$-r amylin (Bolton-Hunter labeled at the N-terminal lysine) may be purchased from Amersham Corporation, Arlington Heights, Ill., aliquoted, and stored frozen until use.

Unlabeled peptides may be obtained from BACHEM Incorporated (Torrance, Calif.) and Peninsula Laboratories (Belmont, Calif.). They are dissolved in sterile water containing protease-free Fraction V BSA, aliquoted, and stored frozen until use.

Reactions are begun by adding membranes to each incubation tube. The amount of tissue (or, more conveniently, the amount of membrane protein) required per tube will be dictated according to the receptor densities of each tissue type. Typically, membranes from about 2.5 mg of tissue (about 100 μg membrane protein) are added.

Reaction mixtures are incubated for a period of time and at a temperature sufficient to reach steady-state conditions within the period. The term "steady state" as used herein is intended to encompass the sum total of all reactions and processes that influence the net amount of bound hormone. It may or may not be synonymous with "equilibrium". Typically, tubes are incubated for about 60 minutes at room temperature.

Membranes are then isolated in order to determine the amount of labeled ligand bound after competition between labeled and unlabeled ligands. It is convenient to collect membranes by filtration with a vacuum-powered Brandel Cell Harvester (Brandel Instruments, Gaithersburg, Md., Model M-24) through glass fiber filters (e.g., GF/B, Whatman) that have been presoaked with a reagent in order to reduce nonspecific binding (NSB). Preferred is presoaking filters for about 5 hours in about 0.3% polyethyleneimine. The skilled artisan will know of other plasma membrane collecting devices, such as the Millipore Filtration Assembly (Model 1225) or the Sandbeck filter box (Bennett, J. P., in *Neurotransmitter Receptor Binding*, H. I. Yamamura et al., Raven, New York 1978, pages 57–90), collecting filters, and NSB-reducing reagents that can be used in practicing this invention. Both immediately before and immediately after filtration, filters are washed with large (milliliter) volumes of ice cold buffer to remove contaminating materials, e.g., unbound labeled peptide hormone. Filters are removed and the amount of labeled peptide hormone bound to plasma membranes is quantified. Where $^{125}I$ is the label, radioactivity may be assessed in a gamma ray counter. Where a chemiluminescent reporter molecule (e.g., AMPPD, Tropix, Inc., Bedford, Mass.) is used, the light produced may be quantified in a luminometer. Enzymatic labels may also be used.

Instead of by filtration, plasma membranes may be isolated following incubation by centrifugation (e.g., Beckman J-2-21-M refrigerated centrifuge at 21,000 rpm or a Beckman 12 or Eppendorf microfuge), washed with ice cold buffer, then counted as such or following solubilization of membranes by detergent or alkali.

Scatchard plot saturation analyses of binding data, wherein bound/free (B/F) labeled peptide hormone is plotted as a function of the amount bound, are performed by standard methods. See, e.g., Blecher 1976, Blecher 1981, Chapter 1, and Boulton et al. 1986, Chapter 1.

Competition curves, wherein the amount bound (B) is plotted as a function of the log of the concentration of ligand (see FIGS. 2–5), may be analyzed by computer, e.g., analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)) Munsun, P. U. and Rodbard, D., *Anal. Biochem.* 107:220–239 (1980).

To determine binding constants, Scatchard saturation curves may be generated and analyzed according to a modification of the method of Scatchard, as described by Bylund, D. B., et al., "Methods for Receptor Binding," in H. I. Yamamura et al., eds., *Methods in Neurotransmitter Analysis*, Raven Press, New York, 1990 pp. 1–35.

In order to obtain specific binding values experimentally, a broad range of tracer concentrations of labeled peptide hormone (typically, 1–150 pM) is used to obtain total binding and duplicate tubes reassessed, in the presence of a very high concentration, e.g., 100 nM, of unlabeled ligand, to obtain nonspecific binding (NSB). The latter value is subtracted from each total binding value in order to obtain specific binding at every concentration of labeled ligand.

The results of the Examples below establish that the method described herein for measuring the ability of peptides to compete against $^{125}I$ labeled amylin, CGRP and calcitonin for binding to specific receptors in membranes from basal forebrain, including nucleus accumbens and surrounding regions, represents a particularly useful means for identifying peptides and other chemical compounds that interact with these receptors. The high density and specificity of receptors in and around the region of the nucleus accumbens result in signal-to-noise ratios (i.e., ratio of specific binding to nonspecific binding) that fall within a useful range for drug screening studies.

The relative potencies of three peptides tested for binding to the $^{125}$I-r amylin receptor site (r Amylin>CGRP>CGRP$_{8-37}$) is disclosed to be similar to their relative potencies in altering soleus muscle glycogen metabolism, and is quite distinct from their ability to compete against $^{125}$I-CGRP for binding to its receptors in liver and soleus muscle membranes. This result is consistent with our determination that the high affinity amylin receptor found in nucleus accumbens area membranes is also present in soleus muscle, albeit at levels not readily detected by current binding methods. The latter tissue is, of course, a target of interest for amylin antagonist and agonist drug development.

The correlation of binding activity with potency in the soleus muscle insulin-antagonism assay demonstrates that the $^{125}$I-r amylin binding assay described above has excellent predictive ability to identify agonists and antagonists of the insulin-opposing actions of amylin and CGRP. The ability of a binding assay using brain tissue to identify the amylin receptor and to identify amylin receptor binding compounds is highly unexpected.

In another aspect, the amylin receptor assay can be used to determine the concentration of amylin or amylin receptor-active compounds in unknown solutions or mixtures. Amylin receptors are assayed as described in Example III below. A membrane or cell preparation containing a high density of amylin receptors, such as the basal forebrain region of rat brain, or a receptor protein preparation, is incubated with radiolabelled amylin and unlabelled amylin at concentrations of $10^{-6}$ as described in Example III. In this manner, a competition curve is generated relating the amount of amylin in the assay tube to the inhibition of radiolabelled amylin binding produced. In additional tubes, unlabelled peptide is replaced by a solution containing an unknown amount of amylin to be quantified. This solution may be plasma, serum or other fluid, or solid mixture dissoved in assay buffers (e.g. HBBP of Example III). The unknown solution is preferably added in a volume of less than or equal to about 10% of the final assay volume, so as not to significantly alter the ionic content of the solution. If larger volumes of unknown are used, a solution containing an equivalent salt content is included as a control for effects of altered ionic content on binding. Nonspecific binding, i.e., binding of radiolabelled amylin in the presence of a high concentration ($10^{-6}$M) of unlabelled amylin or salmon calcitonin, is substracted from total binding for each sample to yield specific binding. The amount of inhibition of specific binding of radiolabelled amylin produced by the unknown is compared to the inhibition curve produced by amylin in order to determine the content of amylin or amylin receptor-active substances in the unknown sample. Methods for performing these calculations are described in several sources, such as in *Neurotransmitter Receptor Binding*, eds H. Yamamura, S. J. Enna, and M. J. Kuhar (Raven Press, New York, 1991).

This method is used to quantitate the amount of amylin-receptor active compounds in a known or an unknown sample, and may be used to quantitate amyinreceptor active compounds in plasma or other body fluids and tissues, for use in identifying active metabolites, pharmacokinetics, stability, solubility, or distribution of amylin, agonists and amylin antagonists. In order to increase the specificity of the assay for amylin where this is necessary, the quantity of CGRP in the unknown sample can be determined through a radio-receptor assay for CGRP. Such a radio-receptor assay can be performed using $^{125}$I-hCGRP and rat liver membranes as described in Example II, with the buffer system described there, according to the methods described for the amylin radio-receptor assay. With this assay, the CGRP content of the unknown sample can be determined. Since the amylin radio-receptor assay identifies all compounds active of amylin receptors, including CGRP, it is useful to subtract CGRP content, as determined by radio-receptor or other assay (e.g. radioimmunoassay) from total content of amylin-receptor active compounds to yield the amount of amylin in samples (e.g. serum) which may contain both amylin and CGRP.

In still another aspect, the amylin receptor is used in a high throughput screen, optionally utilizing robotic systems such as those known in the art, for identifying compounds which displace amylin from its receptor and, thus, identifying candidate amylin agonists or antagonists. The assay can be used to screen, for example, libraries of synthetic compounds, extracts of plants, extracts of marine organisms, or bacterial or fungal fermentation broths. In one embodiment, an initial step brings together about 50 μl of the amylin receptor preparation described above, pre-incubated with about 10 to about 15 pM $^{125}$I Bolton-Hunter rat amylin as described above, and approximately 50μl of the solution of test compound, in assay buffer containing, for example, up to 10% ethanol, or 1% DMSO, or 5% acetonitrile to facilitate dissolution of compound, if required. For organic extracts, the final concentration of solvent should generally not exceed that which displaces the standard displacement curve of labelled amylin by cold amylin by 25%, i.e. shifts the measured IC$_{50}$ by less than 25%. This can be evaluated for each selected solvent. For identified compounds from synthetic libraries, the test concentration will be about 100 nM, 1 μM, or 10 μM depending on the frequency with which positive tests occur. A positive will typically be represented by at least about a 20% reduction of specific binding of labelled amylin. With broths and extracts, a positive test will be denoted by at least about 20%, 50% or 80% reduction in specific amylin binding, according to the frequency of positive tests.

It is useful in high throughput screening to check compounds or mixtures giving a positive test in an initial screen for non-specific interference with ligand binding. In a preferred embodiment, all positive testing compounds or extracts are exposed to a binding assay for another ligand in the same membrane preparation. A suitable assay for evaluating non-specific specific effects will be radiolabelled spiperone or other standard reagent for determination of dopamine (D$_2$) receptor binding. Hess et al., *J. Pharmacol. Exp. Ther.* 238:846-854 (1986). D$_2$ receptors are relatively abundant and readily assayed in basal forebrain. Alternatively, radiolabelled haloperidol can be so used as the ligand for dopamine receptors. Any compound, broth, or extract that tests positive in the amylin receptor screen and which also tests positive by the same quantitative criteria in the dopamine receptor screen is rejected as non-selectively interfering with ligand binding to membrane receptors.

Further aspects of this invention include determination of the interaction with CGRP receptors of compounds, broths or extracts which selectively reduce amylin binding. Thus, steps similar to those described above are undertaken with a binding assay consisting of liver cells or membranes pre-incubated with about 10 to 15 pM $^{125}$I-his$_{10}$-h α-CGRP. Using the quantitative criteria specified above for the amylin assay, compounds, broths or extracts which interact with both amylin and CGRP receptors are identified as those selectively acting at amylin receptor but not at the CGRP receptor.

For compounds meeting described criteria, the potency of interaction with the amylin receptor and, if relevant, the CGRP or calcitonin receptors, are determined by measuring the displacement of ligand from the membrane preparations by a range of concentrations of the test compound. With mixtures of unknown compounds, as in broths and extracts, the desired activity is isolated and purified by art-known methods including HPLC, followed by testing the separated materials to determine which retain the desired activity. When pure or relatively pure active material is obtained, its potency at the amylin, and CGRP receptor can be determined. Art-known methods including NMR, mass spectyroscopy, and elemental analysis may be used to make a chemical identification of any isolated material having the desired receptor binding activities.

At any desired stage following identification of selective displacement of amylin from its receptors, a positive testing material can be assessed in a functional assay to assess amylin agonist activity through, for example, inhibition of insulin-stimulated incorporation of labelled glucose into glycogen in rat soleus muscle. The material can also be tested for antagonist activity in this assay by assessing its ability to restore insulin-stimulated incorporation of labelled glucose into glycogen in rat soleus muscle incubated with 10, 20, 50 or 100 nM rat amylin. Also, by applying different concentrations of the test material in these assays, the potency of amylin agonist or antagonist action can be determined.

Another test of amylin agonist action uses the measurement of elevation of plasma lactate and/or glucose in, for example, halothane-anaesthetized, 18-hour fasted rats following intravenous bolus injections of the test material. By using a series of concentrations, the potency of the material as an amylin agonist can be determined. In a related assay for antagonist activity the test material is infused intravenously into 18-hour fasted, anaesthetized rats. The reduction (compared to control conditions) of the hyperlactemic and/or hyperglycemic response to intravenous injections of a known amount of amylin agonist is then measured or otherwise evaluated. The antagonist potency of such materials can be determined by repeating the test at different infusion rates of the test material.

In other embodiments, for assessment of whether materials testing positive in the amylin receptor binding assay are agonist or antagonists, the test materials are brought together with amylin-responsive membrane or cell systems in which amylin changes rates of synthesis of cyclic AMP. Such preparations include membranes prepared from cultured cell lines with abundant amylin receptors, or the cells themselves. Changes in cAMP levels are measured by radioimmunoassay following exposure of the membrane or cell preparations, incubated according to art-known methods. Materials testing positive in displacing amylin from its receptors and having no effect on cAMP production can be expected to be amylin receptor antagonists. Antagonist action can be further evaluated by incubating various concentrations of the material analog with amylin or an amylin agonist and measuring the degree of inhibition of the changes in cAMP evoked by amylin or an amylin agonist.

In another aspect, the invention is used to screen cell lines, cells disaggregated from tissue, and cells from human or animal blood for amylin receptors. These cells will be used as a readily available source for additional amylin receptor prepartions for development of agonists and antagonists of amylin receptors. Membranes from cells are obtained by homogenization of cells with an instrument such as Polytron (Brinkman Instruments) followed by centrifugation. Membranes so obtained are combined with $^{125}$I-rat amylin in a buffer system such as that described in Example III, and are incubated and collected as described in that Example. Specific binding of $^{125}$I-rat amylin to the cell membrane is identified by measuring the decrease in binding obtained in the presence of, for example, $10^{-7}$M rat amylin or $10^{-7}$ M salmon calcitonin. Cells in which there is a significant difference between total binding (triplicate tubes) and nonspecific binding (triplicate tubes) at the $P<0.05$ level will be used for further study of amylin receptor function.

The previously described amylin receptor binding assay can also be used to further purify amylin receptors from membranes containing these receptors. Membranes are obtained as described in Example III from an area, for example, brain nucleus accumbens, shown to contain a high density of amylin receptors. Subcellular membrane fractions obtained by differential or density gradient centrifugation are assayed for specific binding of radiolabeled amylin in order to identify the membrane fraction containing the highest density of amylin receptors per milligram protein (as assayed by Bradford or Lowry protein assays). The membrane fraction with highest receptor density is preferably used for further purification.

This membrane fraction is collected and treated in a buffered solution with several membrane solubilizing agents, including triton, digitonin, octyl glucoside, deoxycholate, and cholate, at concentrations of from 0.001% to 1% detergent at reduced temperature (4° C.) for about 1 hour. Protease inhibitors (including phenylmethylsulfonyl fluoride, EDTA, aprotinin) are included in the buffer system to prevent receptor degradation during or after solubilization. After treatment of membranes with detergents, unsolubilized membranes are sedimented by centrifugation at high speed (100,000×g for 1 hour) and resulting supernatants containing solubilized receptors are assayed for binding of radiolabeled metolazone as described above. Solubilized receptors can be collected by filtration on polyethyleneiminecoated filters (Bruns, R. F., et al. Anal. Biochem. 132:74-81 (1983). Alternatively, solubilized receptors are collected by methods such as precipitation with polyethyleneglycol, gel filtration, or equilibrium dialysis. Binding characteristics (such as affinity for amylin, CGRP and calcitonins) of solubilized receptors are assessed and should match the characteristics of membrane-localized receptors.

After determining conditions suitable for solubilizing amylin receptors and for assaying solubilized receptors, these solubilized receptors are purified away from other solubilized membrane proteins by chromatographic procedures, such as affinity chromatography on supports to which amylin has been coupled, ion exchange chromatography, lectin agarose chromatography, gel filtration, and hydrophobic interaction chromatography. Chromatography column eluates are tested for specific amylin receptor binding to protein content, in order to identify peaks containing receptors and the extent of purification. Before inclusion in the final purification protocol, each chromatographic step is tested to determine the extent to which it contributes to receptor purification, as measured by an increase in specific radiolabeled amylin binding per milligram protein. Desired chromatography steps are combined sequentially, using large quantities of starting material, in order to obtain partially or completely purified amylin receptors, as desired.

Receptors which have been partially or completely purified by this method are used to generate amylin receptor-specific antibodies for use in diagnosis (disease states with altered amylin receptor density, distribution, or antigenicity) and for use in screening recombinant libraries for amylin receptor expression. Purified receptor preparations can also be used to obtain partial sequence information, which is useful in preparing oligonucleotide probes for screening recombinant libraries for amylin receptor-encoding gene sequences.

Specific embodiments of the receptor binding assay screening method of this invention are exemplified in the following Examples. These Examples are not to be interpreted as limiting the scope of the invention in any way, the scope being disclosed in the entire specification and claims.

EXAMPLE I

PREPARATION OF MEMBRANES

Membranes were prepared from male Wistar or Sprague-Dawley rats (200-250 grams). Following decapitation, liver, soleus muscle and brain regions were removed to phosphate-buffered saline (PBS), pH 7.4 at 4° C. Tissues were weighed then placed in 5 ml/g tissue of ice-cold 20 mM HEPES buffer, pH 7.4, and homogenized with a Polytron at setting 4 for 10 seconds. An additional 30 ml of cold HEPES was added, and the homogenates centrifuged for 15 minutes at 48,000×g. After discarding the supernatant fluids, membrane pellets were homogenized in 40 ml of fresh HEPES buffer and centrifuged as before. Membranes were washed again by homogenization in buffer and centrifugation.

The final membrane pellet was resuspended in a volume of 20 mM HEPES buffer containing 0.2 mM PMSF added immediately before use from a stock 0.2 M solution in ethanol. A volume of buffer was used sufficient to yield a concentration of about 0 to about 20 mg original tissue/ml.

EXAMPLE II

Binding Assays of Amylin and CGRP

To 12×75 mm glass or polypropylene tubes were added 150 μl of HBBM buffer (20 mM HEPES buffer, pH 7.4, containing 1 mg/ml bacitracin, 1 mg/ml protease-free BSA Fraction V, 4 mM $MgCl_2$) to which 0.2 mM PMSF was added just prior to use.

To this solution, 50 μl of unlabeled peptide diluted in HBBM buffer at concentrations of $10^{-11}$ μl to $10^{-6}$ M, were added. Control tubes contained HBBM alone. To this solution was added 50 μl of HBBM containing 5-7 fmol of $^{125}$I-h CGRP or $^{125}$I-r amylin. Incubations were begun by the addition of 250 μl of buffer containing membranes from 4 mg original weight of tissue, and continued for 60 minutes at room temperature (24° C.).

Suspensions were then filtered through GF/B glass fiber filters (previously soaked for 5 hours in 0.3% PEI) in a Brandel M-24 harvester. Filters were washed immediately before use with 5 ml of cold PBS, and immediately after filtration with 15 ml cold PBS. Filters were then counted in a gamma-counter.

Binding of $^{125}$I-h CGRP was measured at 1-150 pM to obtain total binding and again in the presence of 100 nM unlabeled h CGRP to obtain nonspecific binding. The concentration of free ligand was derived by subtracting total binding from total ligand added.

Scatchard and competition curve analysis was performed as described above.

Liver Membranes

Figure 1:
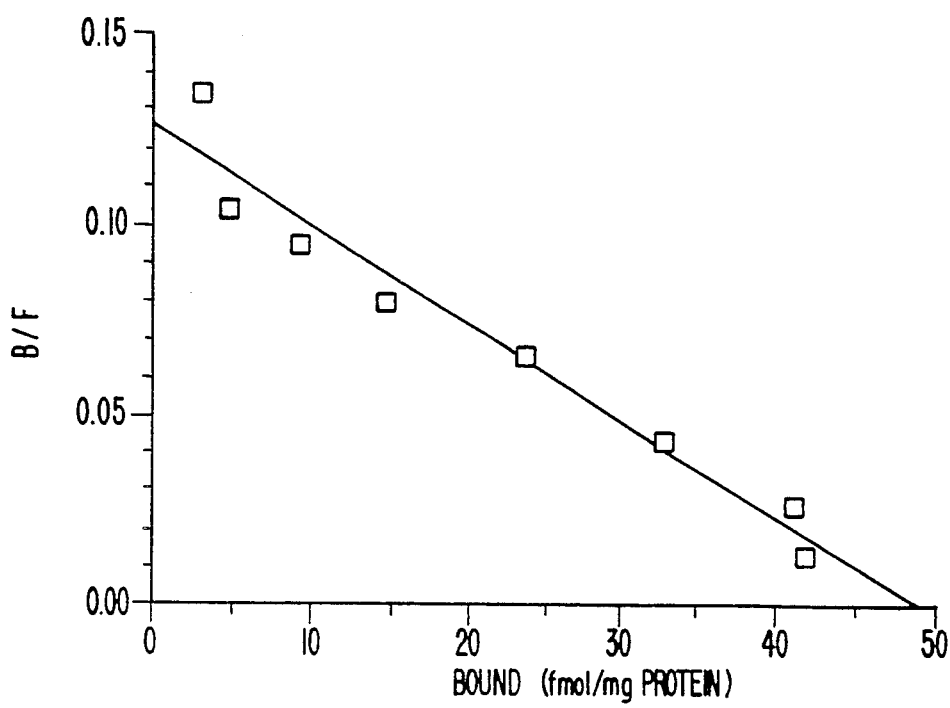
Figure 2:
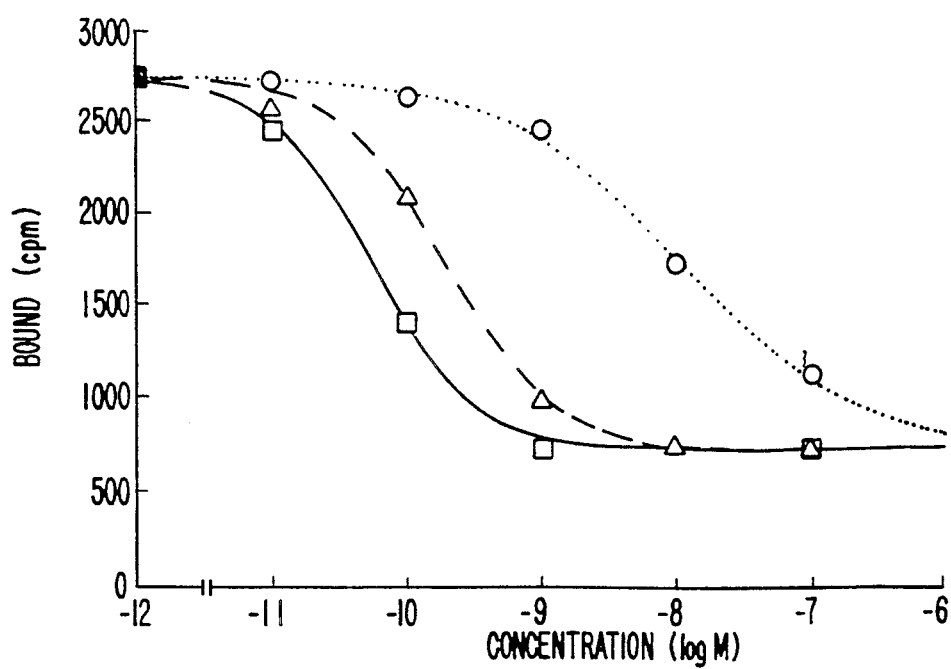
FIG. 2 shows competition binding curves for the binding of human CGRP (open square), human CGRP (fragment 8-37) (open triangle), and rat amylin (open circle) to rat liver membranes, using $^{12}$I-h CGRP as tracer.
Figure 3:
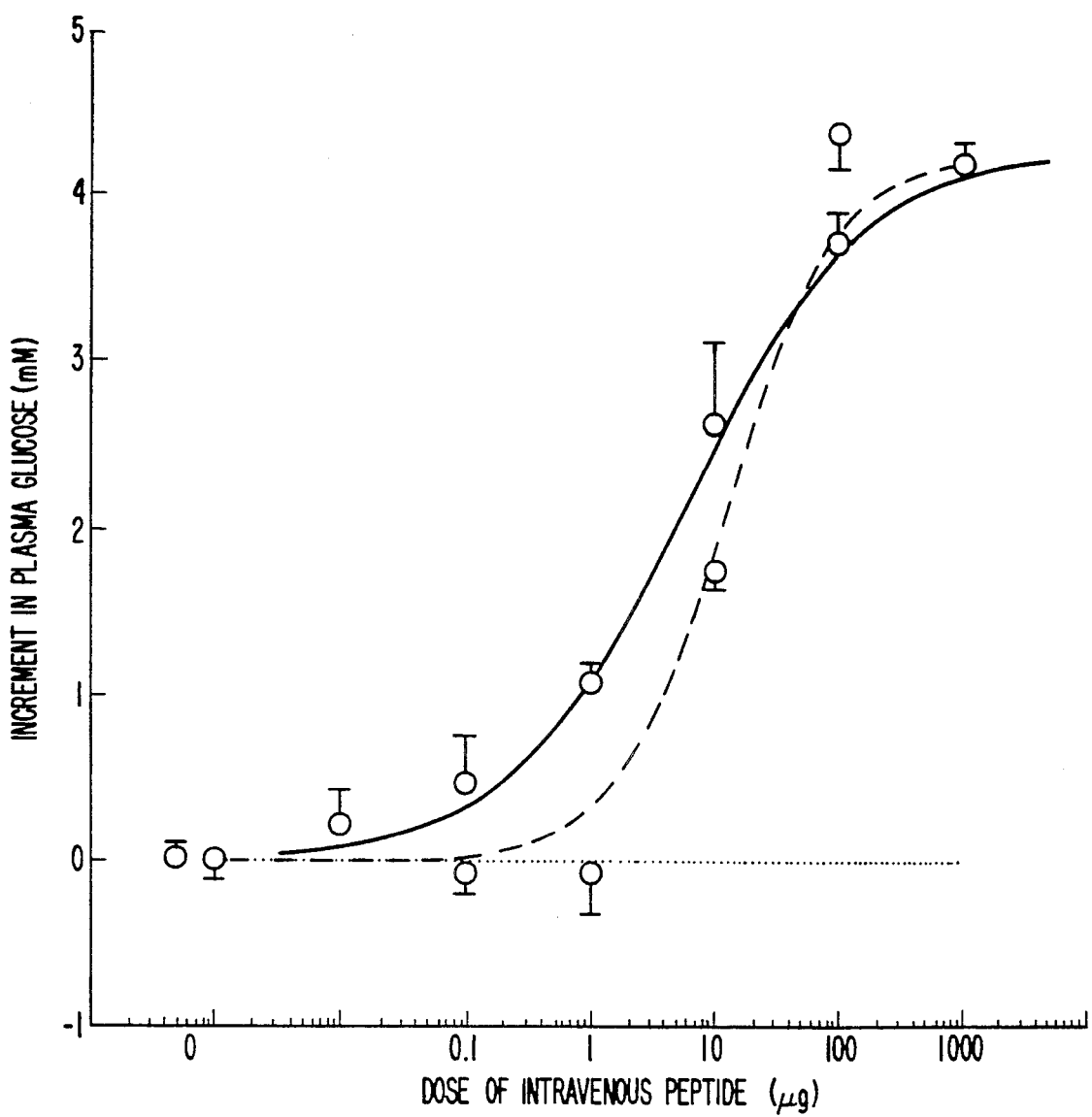
FIG. 3 shows the increments in plasma glucose produced by administration of amylin (solid line) or h CGRP (broken line) (0–1,000 μg i.v.) to fasted anesthetized rats.

The binding of 1.3-150 pM $^{125}$I-h CGRP to rat liver membranes was measured in the absence and presence of $10^{-7}$M h CGRP to generate a saturation curve. Scatchard analyses of this data yielded a single apparent binding site with the following kinetic constants: Kd=19.1 pM and Bmax=49.4 fmol/mg protein (FIG. 1).

Competition curves (FIG. 2) indicated that the profile of the binding site was h CGRP>h $CGRP_{8-37}$>r amylin, with the $IC_{50}$ and Hill slope values shown in Table 1:

TABLE 1

| Peptide | $IC_{50}$ (nM) | Hill Slope |
|---|---|---|
| h CGRP | 0.052 | −1.14 |
| h $CGRP_{8-37}$ | 0.191 | −1.08 |
| r Amylin | 10.5 | −0.67 |

Binding of $^{125}$I-CGRP to liver membranes was increased about 2.8-fold in the presence of 2 mM $MgCl_2$.

No specific binding of 15 pM $^{125}$I-r amylin to rat liver membranes was detected under these conditions, with either 1 μM h CGRP or 1 μM r amylin as the displacing peptide.

L6 Myocyte Membranes

These membranes exhibited a 1$^{125}$I-h CGRP binding site with a pharmacological profile identical to that measured in liver membranes, i.e., CGRP>$CGRP_{8-37}$>amylin, reflecting the determination that the peptide receptor in this tissue, as in liver membranes, does not simulate the receptor-mediated amylin effects upon glycogen metabolism in soleus muscle [amylin≧CGRP≧$CGRP_{8-37}$]. This receptor is useful, however, in screening methods for CGRP agonists and antagonists, or for identifying amylin agonists and antagonists that are selective, in whole or in part, for the amylin receptor.

Rat Soleus Muscle Membranes

These membranes also exhibited a specific $^{125}$I-h CGRP receptor site. The potency of r amylin at competing for this binding site ($IC_{50}$=6.2 nM) was similar to its potency (10.5 nM, Table 1) at competing for $^{125}$I-h CGRP sites in liver membranes.

When labeled r amylin was tested directly with these membranes, a very low density of specific binding sites was obtained (0.009 fmol/mg tissue at 10 pM $^{125}$I-r amylin), and only a small proportion of the total binding (15%) was displaceable by 1 μM unlabeled r amylin.

The experiments with rat liver and rat soleus muscle membranes indicate that the major receptor population detectable using $^{125}$I-h CGRP under the conditions specified has a binding affinity (Ki) for r amylin of 6-10 nM. CGRP is 4 times as potent as h $CGRP_{8-37}$ and about 200fold more potent than r amylin at this receptor, as measured in liver membranes. This affinity is not consistent with the receptor mediating amylin effects upon glycogen metabolism in soleus muscle at which amylin is more potent than CGRP (Leighton et al. 1988; Young et al., Amylin Corporation (unpublished)).

Nor is it consistent with the potency ratio for amylin and CGRP injected into fasted anesthetized rats to cause hyperglycemia. At doses of 1 and 10 μg, amylin is the more effective hyperglycemic agent (FIG. 3), i.e., amylin appears to be more potent at the relevant receptor site. The CGRP binding site measured in these experiments is therefore more likely to represent the receptor mediating vasodilatory actions, rather than insulin antagonistic actions produced by CGRP and amylin.

EXAMPLE III

Binding Assays with Brain Membranes

From the ventral surface of rat brains, cuts were made rostral to the hypothalamus bounded laterally by the olfactory tracts and extending at a 45 angle medially from these tracts. This tissue, containing the nucleus accumbens and surrounding regions, was collected and weighed, and membranes prepared as described in Example I. The region from which tissue was collected as described above is here termed the basal forebrain, and includes the nucleus accumbens and surrounding regions.

$^{125}$I-h CGRP

Binding assays were carried out as described in Example II. In contrast to the results with rat liver membranes, inhibition of the binding of $^{125}$I-h CGRP to nucleus accumbens and surrounding regions was clearly biphasic (FIG. 4B), with IC$_{50}$ values for the 2 sites of 26 pM and 5.9 nM, respectively (Table 2).

TABLE 2

| Peptide | Cerebellum | | Nucleus Accumbens Area | |
|---|---|---|---|---|
| | IC$_{50}$ (nM) | Hill Slope | Peptide | IC$_{50}$ (nM) |
| h CGRP | 0.029 | −1.21 | h CGRP | 0.03 |
| r amylin | 4.9 | −0.897 | r amylin (2 site) | 5.89 (57%) 0.026 (46%) |

Figure 4A:
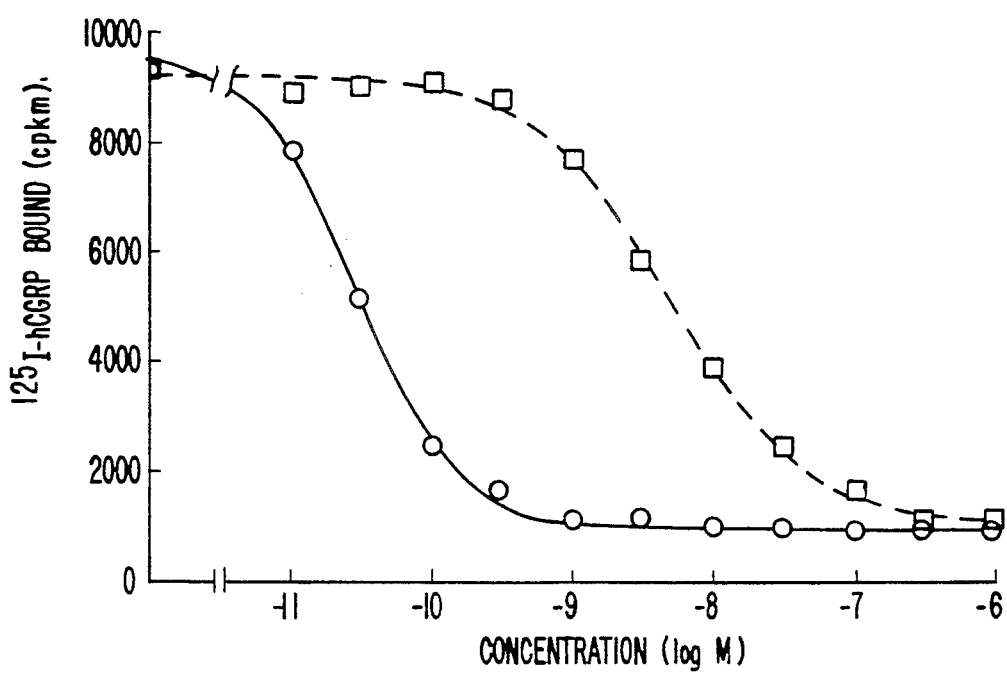
FIG. 4A shows competition curves for the competition of h α-CGRP (open circle) and r amylin (open square) for $^{125}$I-CGRP binding sites in membranes derived from rat cerebellum.
Figure 4B:
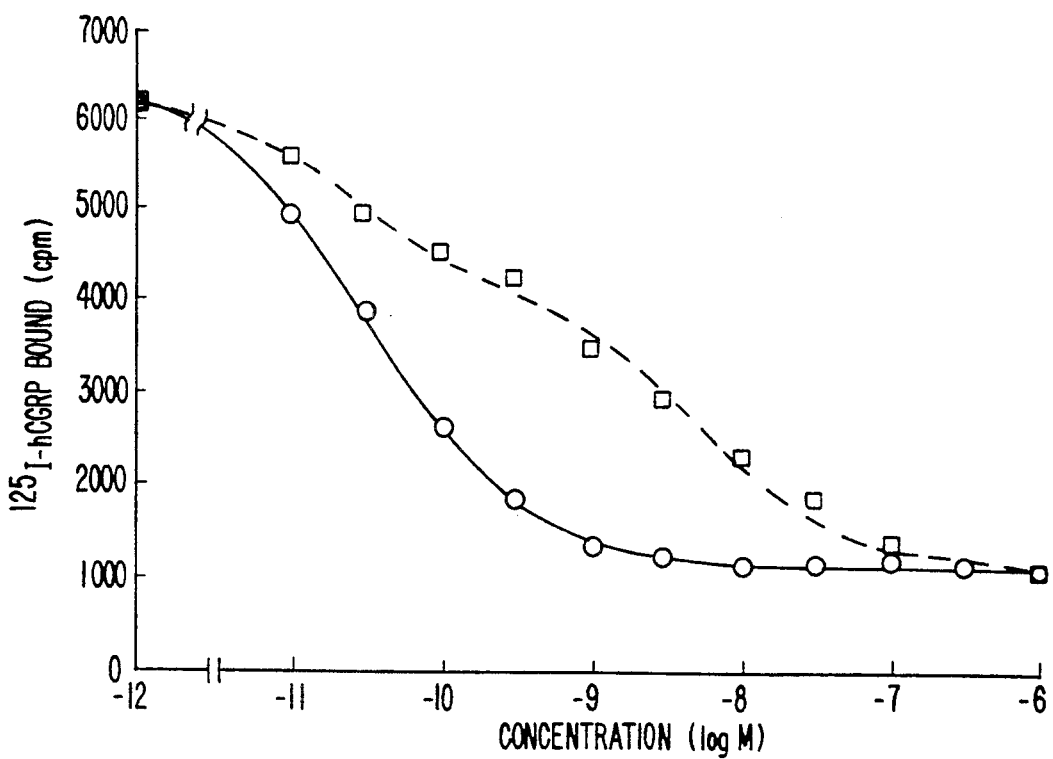
FIG. 4(B) shows the competition curves for FIG. 4(A) using membranes derived from rat basal forebrain.

Cerebellum membranes were also tested, as this area contains high densities of CGRP receptors but low to absent amounts of the variant CGRP receptor subtypes present in nucleus accumbens (Sexton et al., 1988). Inhibition of $^{125}$I-h CGRP binding to cerebellum exhibited only the site with lower affinity (5 nM) for amylin (FIG. 4A and Table 2).

$^{125}$I-r amylin

After demonstrating the high affinity of amylin for one subpopulation of receptors labeled by $^{125}$I-h CGRP in the nucleus accumbens area, we tested the ability of $^{125}$I-r amylin to bind to membrane receptors from this region of rat brain. For these experiments, a smaller assay volume was used, and MgCl$_2$ was omitted from the incubation mixture, as preliminary experiments showed that Mg$^{2+}$ reduced binding of $^{125}$I-r amylin. Buffer identical to HBBM (as in Example I) but without MgCl$_2$ is designated HBBP (HEPES, Bacitracin, BSA, PMSF).

Basal forebrain membranes were prepared from Wistar or Sprague-Dawley rat brains as described above. Following centrifugation of tissue homogenates, the final membrane pellet was resuspended in a volume of 20 mM HEPES buffer (without PMSF) sufficient to yield a concentration of 50 mg original tissue/ml.

Competition curves were generated by the following method. To 12×75 mm polypropylene tubes, 0.1 ml of HBBM buffer mixture and 20 μl of unlabeled peptide at concentrations of 10$^{-11}$ to 10$^{-6}$M in HBBP were added. Control tubes contained HBBP buffer alone. Subsequently, 30 μl containing 3 fmol of $^{125}$I-r amylin in HBBP was added, and the reaction started by addition of 50 μl containing membrane from 2.5 mg original weight of tissue. Incubations were conducted and reaction mixtures were worked up as described in Example II.

For saturation binding experiments, binding of $^{125}$I-r amylin to nucleus accumbens membranes was measured at 1, 2, 4, 9, 18, 35, 70 and 140 pM to obtain total binding, and again in the presence of 100 nM unlabeled salmon calcitonin to obtain nonspecific binding. Scatchard plots of saturation isotherm data were monophasic (FIG. 5). Binding constants for this site were: Kd=27.1±2.1 pM; B$_{max}$=0.976±0.096 fmol/mg tissue (mean±SEM). These findings support our discovery that basal forebrain tissue, including the nucleus accumbins and surrounding regions, contains receptors that bind amylin with high affinity and with high binding site density.

The pharmalogical profile of these receptors was assessed by measuring the ability of several unlabeled peptides to compete for $^{125}$I-amylin binding to rat basal forebrain membranes. $^{125}$I-amylin was present in incubations at a concentration of 14 pM, and peptides were tested at 10 concentrations varying from 10$^{-11}$M to 10$^{-6}$M. Inhibition constants (K$_i$) are presented in Table 3, and were calculated from the IC$_{50}$s according to the Chang-Prusoff equation (*Biochem. Pharmacol.* 22:3099–3108 (1973)) using a value of 27.1 pM for the K$_d$ of $^{125}$I-amylin.

TABLE 3

| Inhibition of $^{125}$I-r amylin binding to rat basal forebrain membranes. | |
|---|---|
| | Ki (pM) |
| rat amylin | 29.1 ± 4.8 |
| eel calcitonin | 35.7 ± 2.6 |
| salmon calcitonin | 39.5 ± 3.0 |
| rat β-CGRP | 83.3 ± 12 |
| human β-CGRP | 148 ± 19 |
| human α-CGRP | 187 ± 13 |
| rat α-CGRP | 405 ± 57 |
| rat calcitonin | >1,000,000 |
| human CGRP$_{8-37}$ | 3100 (n = 1) |

Results are means ± standard errors 3-5 separate experiments using ten concentraions of each peptide varying from 10$^{-11}$ to 10$^{-6}$ M.

Results indicate that rat amylin was the most potent compound tested, with a K$_i$ agreeing very closely with the K$_d$ (27.1 nM) obtained from Scatchard analysis of saturation curves. Eel and salmon calcitonin were slightly less potent than amylin. Rat and human β-CGRP were 3-fold and 5-fold less potent than amylin, while α-CGRPs were somewhat less potent than the β-CGRPs. Rat calcitonin was a very weak inhibitor, indicating that this receptor does not respond to the calcitonin circulating in the rat.

The higher affinity of amylin than CGRP for this receptor correlates with the relative potencies of these peptides at inhibiting glycogenesis in isolated soleus muscle. The high affinity of eel and samon calcitonin suggested the surprising possibility that teleost calcitonins could be potent inhibitors of insulin-stimulated glycogenesis (see Example V).

In order to further evaluate the ability of the amylin receptor assay described above to identify antagonists of the glucoregulatory actions of amylin, h CGRP$_{8-37}$ was tested as a competitive inhibitor. This truncated analogue of h CGRP has been shown to antagonize the insulin-inhibitory actions of amylin in soleus muscle, as described below. The K$_i$ of h CGRP$_{8-37}$ for $^{125}$I-r amylin binding to nucleus accumbens was 3 nM. This amylin receptor assay, therefore, demonstrates that h CGRP$_{8-37}$ has a moderate affinity for neural amylin receptors and predicts that this peptide will be effective when present at concentrations approximately 100-fold greater than amylin. As described below, the pharmacological profile of the amylin receptor measured by the assay of the invention is consistent with the profile of the receptor mediating the inhibition of insulin-stimulated glycogenolysis in skeletal (e.g., soleus) muscle.

EXAMPLE IV

Distribution of Amylin Receptors in Brain

Binding of $^{125}$I-r amylin (17 pM) to membranes isolated by the method of Example III from brain regions pooled from 3 Sprague-Dawley rats was determined by the receptor-based assay of Example II. Nonspecific binding was measured in the presence of $2.5 \times 10^{-8}$ M unlabeled r amylin. The values shown in FIG. 6 represent the mean±SEM of triplicate tubes using a single tissue sample.

The nucleus accumbens and surrounding area contained the highest density of receptors for r amylin (FIG. 6).

EXAMPLE V

Predictive Utility of Receptor Assay

One use of the amylin receptor binding assay is in the identification of compounds that can affect amylin/insulin effects via an action at amylin receptors. Teleost calcitonins were evaluated for their ability to bind to the amylin receptor in the nucleus accumbens area membrane assay, and a high affinity for the amylin receptor was discovered (Example III). These unexpected results led to our determination that these peptide hormones could be potent agonists or antagonists at amylin receptors in skeletal muscle. Accordingly, eel and salmon calcitonins were tested in the rat soleus muscle insulin-antagonism assay.

The ability of insulin to stimulate glycogen synthesis in rat soleus muscle in vitro was measured as described by Leighton B. and Cooper, G. J. S., *Nature* 335:632–635 (1988), with the following modifications. Rats were unfed for 4 hours prior to sacrifice; muscles were not stretched on clips; bovine serum albumin (BSA) and HEPES were omitted from the assay medium; and, the insulin concentration used was 1000 μU/ml.

r Amylin inhibited the stimulation of glycogen synthesis by insulin with an IC$_{50}$ of 8.3±1.9 nM (mean±SEM for 6 experiments). The IC$_{50}$ of h α-CGRP producing this effect was 24 nM (mean of 2 experiments), i.e., 3-fold less potent. The IC$_{50}$ of eel calcitonin was 0.4 nM and the IC$_{50}$ of salmon calcitonin was 0.38 nM. The results indicated that both eel and salmon calcitonins were potent agonists at amylin receptors in rat skeletal muscle, as they both effectively reduced insulin-stimulated glycogenesis in this tissue at subnanomolar concentrations. This finding provides further strong evidence of the usefulness of the receptor-based screening assay inventions for identifying compounds active at an amylin receptor that mediates glucoregulatory effects in peripheral tissues.

The effects of h CGRP$_{8-37}$ in the rat soleus muscle glycogenesis system were measured according to the following method. Insulin stimulated glycogen synthesis was measured as described above in the presence of 100 nM rat amylin to maximally suppress glycogen synthesis. Increasing concentrations of hCGR$_{8-37}$ were added to test its ability to antagonize amylin, i.e., to increase glycogen synthesis under these conditions. The results demonstrated that this truncated analogue of h CGRP antagonized the effects of 100 nM amylin on insulin-stimulation glycogenesis in skeletal muscle with an IC$_{50}$ of 6.6±0.9 μM (mean±SEM of 4 experiments). This value is about 800-fold higher than the EC$_{50}$ of r amylin itself. r Amylin was present at a concentration 12-fold above its EC$_{50}$ in the soleus assay, indicating that hCGRP$_{8-37}$ has approximately 70-fold lower affinity than r amylin at the relevant receptor in skeletal muscle. This result is consistent with the relative affinity of h CGRP$_{8-37}$ and rat amylin as demonstrated in the amylin receptor assay, in which hCGRP$_{8-37}$ is 100-fold less potent than r amylin (Example III).

It was observed that all peptides tested had a measured lower potency in the rat soleus muscle assay than in the isolated membrane receptor binding assay, which may be due at least in part to limited access of exogenously presented peptides to all of the cells of intact soleus muscle, to increased metabolism of peptides by muscle proteases of intact tissues at 37° C., and to lower effective affinity of ligands for receptors on intact cells than in membrane fragments.

We claim:

1. An assay method for use in identifying or screening for compounds which inhibit the binding of amylin to amylin receptors, which comprises the steps of:
   (a) bringing together a test sample and an amylin receptor preparation, said test sample containing one or more test compounds, and said amylin receptor preparation comprising an isolated cell or membrane preparation containing amylin receptors capable of detectably binding amylin and having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with an amylin ligand for binding to said amylin receptor preparation;
   (b) incubating said test sample and said amylin receptor preparation under conditions which would permit the binding of amylin to said amylin receptors; and,
   (c) determining the presence or amount of binding between said test sample and said amylin receptor preparation in order to identify those test samples containing one or more test compounds which detectably bind to said amylin receptors.

2. The assay method of claim 1 which further comprises, (d) screening said test samples which detectably bind to said amylin receptors for in vitro or in vivo stimulation or inhibition of amylin-mediated activity; and, (e) determining the presence or amount of stimulation or inhibition of amylin-mediated activity in order to identify those test samples which act as agonists or antagonists of amylin.

3. The assay method of claim 2 wherein said test samples which detectably bind to said amylin receptor protein are identified by measuring the displacement of a labelled first ligand from said amylin receptor preparation by said test sample, and comparing the measured displacement of said first labelled ligand from said amylin receptor preparation by said test sample with the measured displacement of said first labelled ligand from said amylin receptor preparation by one or more known second ligands.

4. The assay method of claim 1 wherein said amylin receptor preparation comprises isolated cells.

5. The assay method of claim 3 wherein said cells bearing said amylin receptor are brain cells.

6. The assay method of claim 5 wherein said brain cells are from the rat basal forebrain.

7. The assay method of claim 1 wherein said amylin receptor preparation comprises a membrane preparation.

8. The assay method of claim 7 wherein said membrane preparation is produced from brain cells.

9. The assay method of claim 8 wherein said brain cells are from the rat basal forebrain.

10. The assay method of claim 1 wherein said test samples which detectably bind to said amylin receptor protein are identified by measuring the displacement of a labelled first ligand form said amylin receptor preparation by said test sample, and comparing the measured displacement of said first labelled ligand from said amylin receptor preparation by said test sample with the measured displacement of said first labelled ligand from said amylin receptor preparation by one or more known second ligands.

11. The assay method of claim 10 wherein said labelled first ligand is amylin.

12. The assay method of claim 11 wherein said amylin is rat amylin.

13. The assay method of claim 12 wherein said rat amylin is $^{125}$I rat amylin.

14. The assay method of claim 10 wherein said labelled first ligand is an amylin agonist.

15. The assay method of claim 14 wherein said amylin agonist is selected from the group consisting of CGRP, salmon calcitonin, and eel calcitonin.

16. The assay method of claim 10 wherein said labelled first ligand is an amylin antagonist.

17. The assay method of claim 16 wherein said amylin antagonist is CGRP$_{8-37}$.

18. The assay method of claim 10 wherein said first ligand is labelled with a member selected from the group consisting of radioactive isotopes, nonradioactive isotopes, fluorescent molecules, chemiluminescent molecules, and biotinylated molecules.

19. The assay method of any of claims 10, 11, 14, 16 or 18 wherein said known second ligand or ligands are selected from the group consisting of amylin, calcitonin, $\alpha$CGRP, and $\beta$CGRP.

20. The assay method of any of claims 10, 11, 14, 16 or 18 wherein said known second ligand or ligands are selected from the group consisting of human amylin, dog amylin, rat amylin, human calcitonin, rat calcitonin, eel calcitonin, salmon calcitonin, human $\alpha$-CGRP, human $\beta$-CGRP, rat$\alpha$-CGRP, and rat $\beta$-CGRP.

21. The assay method of any of claims 1, 2 or 10 wherein said test sample comprises one or more known test compounds.

22. The assay method of any of claims 1, 2 or 10 wherein said test sample comprises one or more unknown compounds.

23. The assay method of claim 1 wherein said compounds which inhibit the binding of amylin to amylin receptors are the agonists or antagonists of amylin.

24. The assay method of any of claims 1, 26, 27, 28, 37 or 38 wherein said mammalian calcitonin is rat calcitonin.

25. The assay method of any of claims 1, 26, 27, 28, 37 or 38 wherein said mammalian calcitonin is human calcitonin.

26. An assay method for use in identifying or screening for compounds which inhibit the binding of amylin to amylin receptors, which comprises the steps of:

(a) bringing together a test sample and an amylin receptor preparation, said test sample containing one or more test compounds, and said amylin receptor preparation comprising an isolated cell or membrane preparation containing amylin receptors capable of detectably binding amylin and having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with an amylin ligand for binding to said amylin receptor preparation;

(b) incubating said test sample and said amylin receptor preparation under conditions which would permit the binding of amylin to said amylin receptors;

(c) determining the presence or amount of binding between said test sample and said amylin receptor preparation in order to identify those test samples containing one or more test compounds which detectably bind to said amylin receptors;

(d) preparing two or more additional test samples from said test sample or samples that are determined to contain one or more test compounds which detectably bind to said amylin receptors, said additional test samples being characterized in that they contain a lesser number of test compounds that said test sample from which they were prepared; and, (e) repeating steps (a)–(d) as many times as desired or until the test compound or compounds which bind to said amylin receptors have been identified.

27. An assay method for use in identifying or screening for compounds which inhibit the binding of amylin to amylin receptors which comprises the steps of, (a) bringing together a test sample and an amylin receptor preparation, said test sample containing one or more test compounds, and said amylin receptor preparation comprising an isolated cell or membrane preparation containing amylin receptors capable of detectably binding amylin and having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with an amylin ligand for binding to said amylin receptor preparation;

(b) incubating said test sample and said amylin receptor preparation under conditions which would permit the binding of amylin to said amylin receptors;

(c) determining the presence or amount of binding between said test sample and said amylin receptor preparation in order to identify those test samples containing one or more test compounds which detectably bind to said amylin receptors;

(d) screening said test samples which detectably bind to said amylin receptors for in vitro or in vivo stimulation or inhibition of amylin-mediated activity;

(e) determining the presence or amount of stimulation or inhibition of amylin-mediated activity in order to identify those test samples which act as agonists or antagonists of amylin, (f) preparing two or more additional test samples from said test sample or samples that are determined to stimulate or inhibit amylin-mediated activity, said additional test samples being characterized in that they contain a lesser number of test compounds than said test sample from which they were prepared; and, (g) repeating steps (a)-(f) as many times as desired or until the test compound or compounds which bind to said amylin receptors have been identified.

28. An assay method for evaluating a known or candidate amylin agonist or antagonist compound for receptor binding selectivity, which comprises the steps of:

(a) bringing togehter said compound, a labelled amylin receptor ligand, and an amylin receptor preparation comprising an isolated cell or membrane preparation containing amylin receptors capable of detectably binding amylin, and determining or measuring the ability of said compound to compete against said labelled amylin receptor ligand for binding to said amylin receptor preparation, said amylin receptor preparation having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with an amylin ligand for binding to said amylin receptor preparation;

(b) brining together said compound, a labelled CGRP receptor ligand, and a CGRP receptor preparation, and determining or measuring the ability of said compound to compete against said labelled CGRP receptor ligand for binding to said CGRP receptor preparation; and/or, (c) bringing together said compound, a labelled calcitonin receptor ligand, and a calcitonin receptor preparation, and determining or measuring the ability of said compound to compete against said labelled calcitonin receptor ligand for binding to said calcitonin receptor preparation; and, (d) comparing the results of steps (a) and (b) and/or (c) in order to determine the receptor binding selectivity of said compound.

29. The assay method of claim 1 wherein said CGRP receptor preparation comprises hepatocytes.

30. The assay method of claim 29 wherein said hepatocytes are comprised of a primary cell culture or an established cell line.

31. The assay method of claim 30 wherein said hepatocytes comprise an established cell line, and said established hepatocyte cell line is the Hep G2 cell line.

32. The assay method of claim 28 wherein said CGRP receptor preparation comprises Hepatocyte membranes.

33. The assay method of claim 28 wherein said CGRP receptor preparation comprises myocytes.

34. The assay method of claim 33 wherein said myocytes are comprised of a primary cell culture or an established cell line.

35. The assay method of claim 28 wherein said CGRP receptor preparation comprises myocyte membranes.

36. The assay method of claim 35 wherein said myocytes comprise an established cell line, and said established cell line is the L6 cell line.

37. An assay method for evaluating a known candidate amylin agonist or antagonist for amylin receptor binding affinity, which comprises bringing together said compound, a labelled amylin receptor ligand, and an amylin receptor preparation, said amylin preparation comprising an isolated cell or membrane preparation containing amylin receptors capable of detectably binding amylin and having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with any amylin ligand for binding to said amylin receptor preparation, and determining or measuring the ability of said compound to compete against said labelled amylin receptor ligand for binding to said amylin receptor preparation.

38. An assay method for determining the presence or amount of any amylin receptor binding compound in a test sample to be assayed for said compound, which comprises the steps of:

(a) bringing together said test sample to be assayed and an amylin receptor preparation, said amylin receptor preparation comprising an isolated cell or membrane preparation containing amylin receptors capable of detectably binding amylin and having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with an amylin ligand for binding to said amylin receptor preparation;

(b) measuring the binding of said test sample to said amylin receptor preparation in the presence of a labelled amylin receptor ligand in order to determine the presence or amount of amylin receptor binding compound in said test sample.

39. The assay method of claim 38 wherein said amylin receptor binding compound is amylin.

40. The assay method of claim 38 wherein said amylin receptor binding compound is an amylin agonist.

41. The assay method of claim 38 wherein said amylin receptor binding compound is an amylin antagonist.

42. The assay method of claim 38 wherein said labelled ligand is amylin.

43. The assay method of claim 38 wherein said labelled ligand is an amylin agonist.

44. The assay method of claim 38 wherein said labelled ligand is an amylin antagonist.

45. The assay method of claim 38 wherein said amylin receptor binding compound is amylin, and said labelled ligand is amylin.

46. The assay method of claim 38 wherein said amylin receptor binding compound is an amylin agonist and said labelled ligand is an amylin agonist.

47. The assay method of claim 38 wherein said amylin receptor binding compound is an amylin antagonist and the labelled ligand is an amylin antagonist.

48. The assay method of claim 38 wherein said test sample is a biological fluid.

49. The assay method of claim 48 wherein said biological fluid is a member selected from the group consisting of blood, plasma, urine, cerebrospinal fluid, and lymph fluid.

50. The assay method of claim 38 wherein said test sample is an amylin preparation.

51. A process which comprises the use of the assay method of claim 38 to evaluate the stability of an amylin preparation.

52. A process which comprises the use of the assay method of claim 38 to evaluate the potency of an amylin preparation.

53. A process which comprises the use of the assay method of claim 38 to evaluate the solubility of an amylin preparation.

54. The assay method of claim 38 which further comprises,
(c) relating the amount of amylin receptor binding compound in said test sample with the amount of amylin receptor binding compound measured for a control sample in accordance with steps (a) and (b), said control sample being known to be free of any amylin receptor binding compound, and/or relating the amount of amylin receptor binding compound in said test sample with the amounts of amylin receptor binding compound measured for control samples containing known amounts of amylin receptor binding compound in accord acne with steps (a) and (b), to determine the presence or amount of amylin receptor binding compound in said test sample.

55. An assay method for use in identifying or screening for compounds which inhibit the binding of amylin or amylin receptors which comprises the steps of:
(a) bringing together a test sample and a receptor preparation, said test sample containing one or more test compounds, and said receptor preparation having a relative ligand binding profile such that the binding potency of amylin and salmon calcitonin to said receptor preparation is greater than the binding potency of CGRP, the binding potency of CGRP to said receptor preparation is greater than the binding potency of a mammalian calcitonin, said binding potency of said ligands being measured by determining the ability of said ligands to compete with an amylin ligand for binding to said amylin receptor preparation;
(b) incubating said test sample and said amylin receptor preparation under conditions which would permit the binding of amylin to said amylin receptors; and,
(c) determining the presence or amount of binding between said test sample and said amylin receptor preparation in order to identify those test samples containing one or more test compounds which detectably bind to said amylin receptors.

56. The method of claim 55 wherein said mammalian calcitonin is rat calcitonin.

57. The method of claim 55 wherein said mammalian calcitonin is human calcitonin.

58. The method of claim 55 wherein said amylin receptor preparation comprises an isolated cell preparation.

59. The method of claim 55 wherein said amylin receptor preparation comprises a membrane preparation.

60. An assay method for use in identifying or screening for compounds which inhibit the binding of amylin to amylin receptors which comprises the steps of:
(a) bringing together a test sample and an amylin receptor preparation, said test sample containing one or more test compounds, and said amylin receptor preparation comprising an isolated receptor protein preparation containing amylin receptors capable of binding amylin;
(b) incubating said test sample and said amylin receptor preparation under conditions which would permit the binding of amylin to said amylin receptors; and,
(c) determining the presence or amount of binding between said test sample and said amylin receptor preparation in order to identify those test samples containing one or more test compounds which detectably bind to said amylin receptors.

61. The assay method of claim 60 wherein said receptor protein is isolated from brain cells.

62. The assay method of claim 61 wherein said brain cells are from the rat basal forebrain.

63. An assay method for use in identifying or screening for compounds which inhibit the binding of amylin to amylin receptors which comprises the steps of:
(a) bringing together a test sample and a receptor preparation, said test sample containing one or more test compounds, and said receptor preparation consisting essentially of amylin receptors capable of binding amylin;
(b) incubating said test sample and said receptor preparation under conditions which would permit the binding of amylin to said amylin receptors; and,
(c) determining the presence or amount of binding between said test sample and said receptor preparation in order to identify those test samples containing one or more test compounds which detectably bind to said amylin receptors.

* * * * *